United States Patent [19]
Fritz et al.

[11] Patent Number: 6,024,138
[45] Date of Patent: Feb. 15, 2000

[54] DISPENSING DEVICE FOR DISPENSING SMALL QUANTITIES OF FLUID

[75] Inventors: Michael Fritz, Biblis; Heinz Macho, Fürth; Helmut Rinkel, Lampertheim; Jürgen Schwab, Ketsch; Georg Arras, Reichelsheim; Klaus Oswald, Riedstadt-Crumstadt; Alfred Schaffner, Brensbach-Höllerbach, all of Germany

[73] Assignee: Roche Diagnostics GmbH, Mannheim, Germany

[21] Appl. No.: 09/061,960

[22] Filed: Apr. 17, 1998

[30] Foreign Application Priority Data

Apr. 17, 1997 [DE] Germany ............................ 197 16 073

[51] Int. Cl.⁷ ........................................................ B65B 1/04
[52] U.S. Cl. .................................. 141/31; 141/9; 141/100; 23/864.01
[58] Field of Search ..................................... 141/26, 31, 9, 141/100, 329, 330, 383, 384, 386; 73/864.01, 864.11, 864.14, 864.85, 864.86; 222/420

[56] References Cited

U.S. PATENT DOCUMENTS

| | | | |
|---|---|---|---|
| 2,965,255 | 12/1960 | Gerarde | 215/6 |
| 3,233,785 | 2/1966 | Burke | 222/158 |
| 3,603,156 | 9/1971 | Konkol | 141/31 |
| 4,393,909 | 7/1983 | Pearson | 141/330 |
| 4,563,104 | 1/1986 | Saint-Amand | 401/139 |
| 5,775,546 | 7/1998 | Buehler | 222/209 |

FOREIGN PATENT DOCUMENTS

| | | |
|---|---|---|
| 30 16 594 A1 | 11/1981 | Germany . |
| 946967 | 1/1964 | United Kingdom . |
| 79/01131 | 12/1979 | WIPO . |
| 96/14017 | 5/1996 | WIPO . |

*Primary Examiner*—Steven O. Douglas
*Attorney, Agent, or Firm*—Nikaido Marmelstein Murray & Oram, LLP

[57] ABSTRACT

Dispensing device for dispensing small quantities of fluid comprising a compressible balloon with an end-to-end capillary inserted within the walls of the balloon in such a way that the one end of the capillary communicates with the interior of the balloon and the other end of the capillary communicates with the exterior space. The balloon has at least one opening through which the interior space of the balloon communicates with the exterior space. The at least one opening has a flow resistance that is designed so that a fluid contained in the capillary is expelled when the balloon is compressed. The present invention also comprises a system and method for the metered dispensing of fluids.

40 Claims, 6 Drawing Sheets

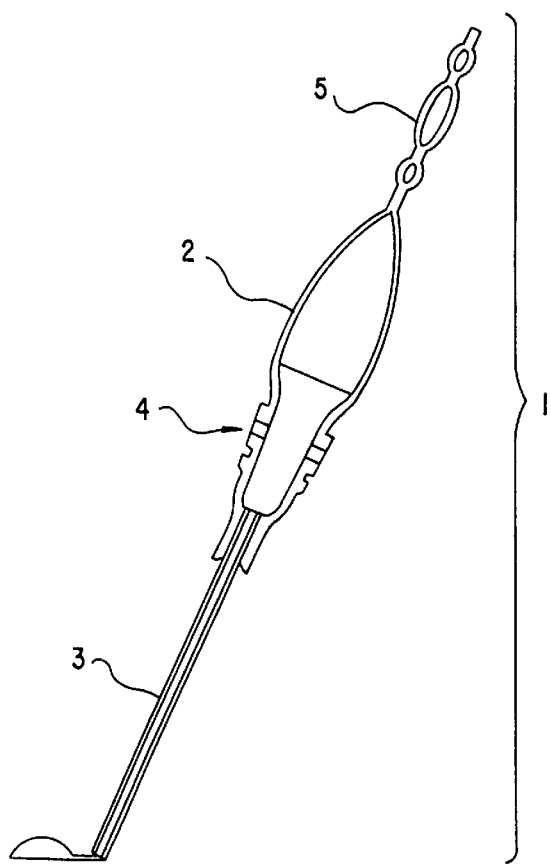
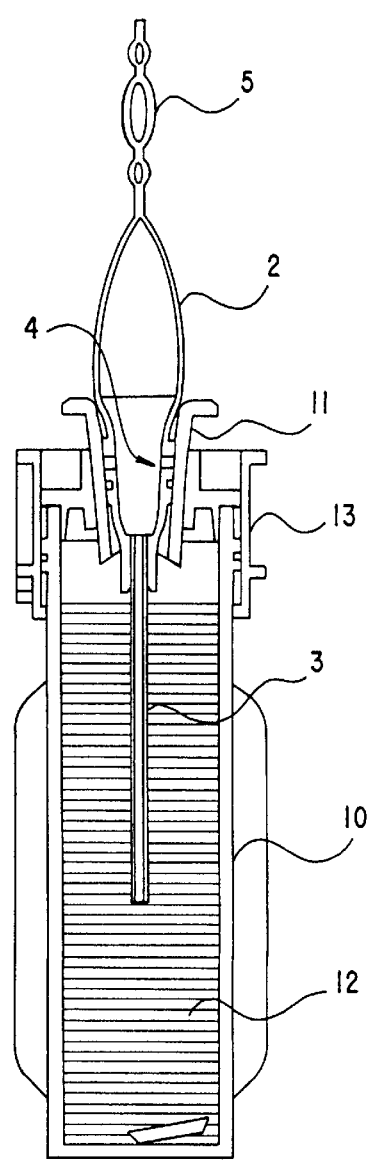

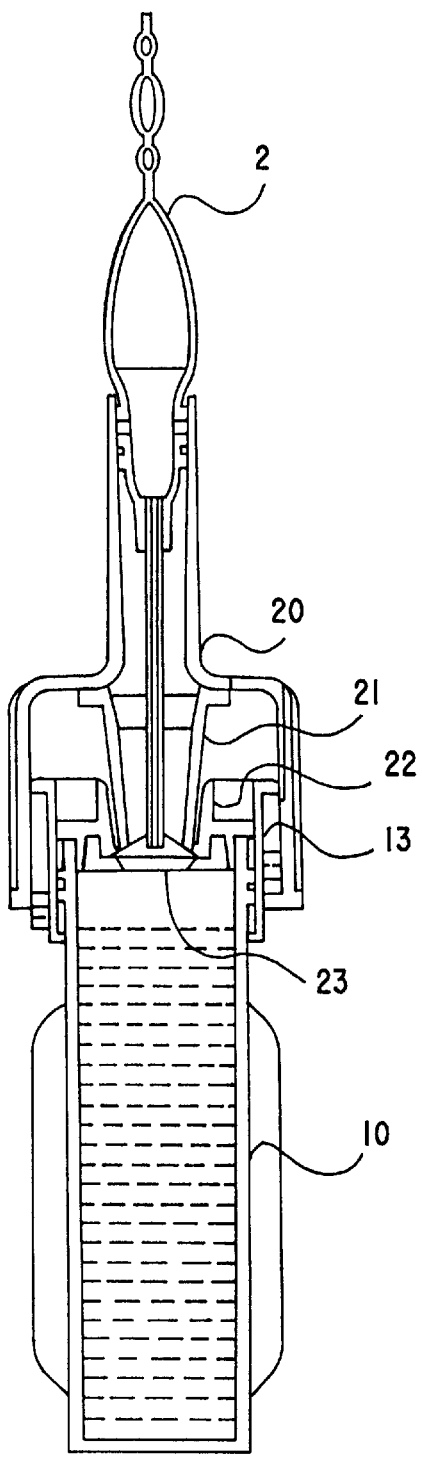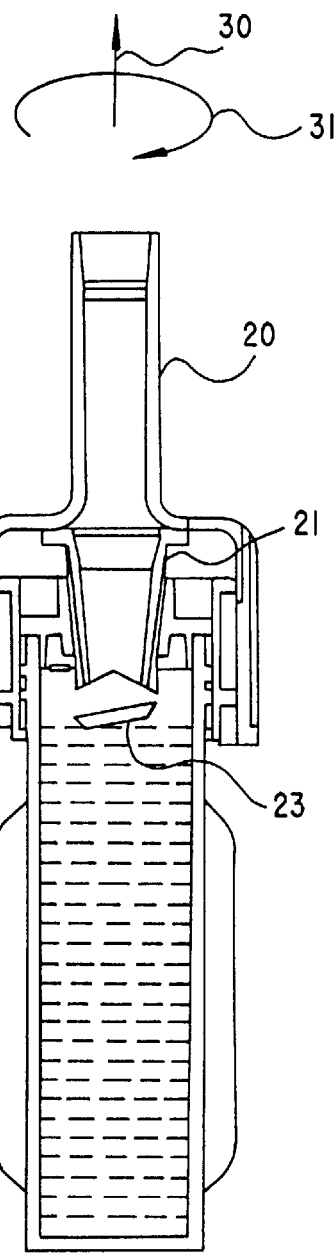

DISPENSING DEVICE FOR DISPENSING SMALL QUANTITIES OF FLUID

FIELD OF THE INVENTION

The present invention provides a dispensing device for dispensing small quantities of fluid comprising a compressible balloon with an end-to-end capillary inserted within its walls in such a way that one end of the capillary communicates with the interior space of the balloon and the other end of the capillary communicates with the exterior space. The balloon also comprises at least one opening through which the interior space of the balloon communicates with the exterior space. The at least one opening has a flow resistance that is designed so that a fluid contained in the capillary is expelled when the balloon is compressed. The present invention also comprises a system for the metered dispensing of sample fluids comprising a dispensing device with a compressible balloon with an end-to-end capillary inserted within its walls and the at least one opening in the balloon through which the interior space communicates with the exterior space. The dispensing device also comprises a vessel with a closure section that has a collar into which the dispensing device can be inserted so that the opening in the balloon is closed by the collar and the end-to-end capillary extends into the interior of the vessel.

The preferred application of the present invention is in the field of clinical chemistry, although it can be used in any application that requires the metered dispensing of small, predetermined quantities of fluid. Such dispensing devices are used in blood testing in particular to determine the number of leukocytes and erythrocyte contained in the blood sample.

DESCRIPTION OF PRIOR ART

According to the standard procedure described in the prior art, the first step in capillary blood testing is to puncture the fingertip, earlobe, or—in the case of a young child—the heel with a lancet and then to collect the blood in an end-to-end capillary. The end-to-end capillary is then placed in a vessel with dilution fluid, the capillary is rinsed by dilution fluid, and the diluted blood sample is then tested, usually using microscopy. In WO 96/14017, a sample collection device is described with which blood tests of this nature can be simplified. A closed vessel containing dilution fluid is opened, and a holding device to which an end-to-end capillary is attached is inserted into the opening. The end-to-end capillary is brought in contact with the sample to be collected and draws up the sample fluid by means of capillary forces. A cap is then placed on the holding device, whereby the internal pressure in the cap increases and the sample fluid is ejected out of the capillary into the vessel containing the dilution fluid. The device and procedure described in WO 96/14017 have serious disadvantages in practice, however, that are described in the document itself. When using this device, the user must make certain that the end of the capillary that extends into the vessel containing the dilution fluid does not touch the fluid, or the capillary will fill with dilution fluid instead of sample. Therefore the device described must be assembled before use, i.e., the user first has to open the vessel containing the dilution fluid and install the holding device. Even the handling of the assembled device is problematic, because the user must be careful not to tip or shake the device to avoid bringing the fluid and capillary in contact with each other. As a result, the sample fluid must be brought in contact with the open end of the capillary from above. Although this is relatively simple to accomplish with a fingertip blood drop, serious handling problems are usually encountered when collecting other sample fluids.

SUMMARY OF THE INVENTION

Object of the present invention, therefore, was to provide a dispensing device for dispensing small quantities of fluid with easy, reliable handling.

The present invention provides a dispensing device with a compressible balloon with an end-to-end capillary inserted within its walls in such a way that one end of the capillary communicates with the interior space of the balloon and the other end of the capillary communicates with the exterior space. The balloon also comprises at least one opening through which the interior space of the balloon can communicate with the exterior space. The size of this opening is designed in such a way to allow air to escape the interior space of the balloon when fluid is drawn into the capillary, so that excess pressure is avoided. To accomplish this, the diameter of the opening must be large enough to prevent excessive flow resistance. On the other hand, the opening must be small enough to allow pressure to be created in the balloon by the flow resistance of the opening when the balloon is compressed to eject all of the sample fluid from the capillary. The technically feasible diameter range for the opening depends on a number of factors. The lower limit of the diameter range is limited more by the potential methods for manufacturing openings of such small size than by the requirement that gas be able to escape from the balloon quickly enough. The upper limit of the diameter of the opening depends on the following factors;

volume of the balloon speed of compression diameter of the capillary and viscosity of the sample fluid. Practical experience has shown that dispensing balloons should have a volume of between 50 $\mu$l and 20 ml, and capillaries should have a volume of between 1 and 200 $\mu$l. Typical internal diameters for the capillaries are between 0.1 and 4 mm. Under the conditions described above, the diameter of the opening in the balloon is preferably between 0.01 and 3 mm$^2$. The compressible balloon of the dispensing device can be made from rubber, cloth, or a metal foil, for instance. The balloon is preferably made of plastic, however, such as polyethylene or polypropylene. When the appropriate plastics are used, the balloon can be manufactured using an injection molding or extrusion procedure. An opening or a channel for holding the capillary can be built in during the manufacturing process, in a similar fashion, the at least one opening can be built into the balloon during the manufacturing process. On the other hand, it is also possible to design the manufacturing process so that an end-to-end capillary is surrounded by plastic using an extrusion process. According to another possible procedure, the balloon can be manufactured first and then an opening can be created in the balloon into which the capillary can be inserted. According to this procedure, the opening with which the interior space in the balloon communicates with the exterior space can be created afterwards, e.g., using a drill or a needle. In an especially preferred embodiment, the opening with which the interior space of the balloon communicates with the exterior space is located next to the exterior surface of the capillary in the form of a channel. This embodiment offers an advantage in that the balloon only needs one opening that is designed so that a channel remains after the capillary is inserted. According to this embodiment, it is also possible to manufacture an opening that is especially small in size. For instance, a thin metal thread can be placed between the capillary and the balloon wall surrounding the capillary, creating a bypass in the form of a small gap.

To simplify handling and improve dispensing accuracy, it has proven to be advantageous to install a viewing window in the balloon through which the end of the capillary that extends into the interior of the balloon can be viewed, enabling the user to determine whether the capillary is completely filled with sample fluid. To prevent a parallax error, the viewing window is preferably situated at the same level as the end of the capillary. The opening that must be created in the balloon anyway can be used as the viewing window. It is also favorable to use a clear plastic for the viewing window, e.g. in form of a transparent circumferential ring around the device axis that is dome shaped and therefore functions as a magnifying glass.

It has proven to be advantageous to provide the dispensing device with a holding device, the handling of which has no effect on the pressure inside the balloon. To draw sample fluid into the capillary, the dispensing device is first held with this holding device in order to prevent the balloon from being compressed accidentally during the collection process. The holding device is preferably connected with the balloon as a single piece, and can be manufactured attached to the balloon in the injection molding or extrusion process.

A method for dispensing fluids using the dispensing device described above comprises the following steps:

The capillary is brought in contact with a sample fluid so that it fills with the sample fluid, the sample fluid contained in the capillary is dispensed via compression of the balloon.

When the capillary is immersed in the sample fluid, sample fluid usually also adheres to the exterior of the capillary. To ensure that an exact quantity of fluid is dispensed, it is therefore advantageous to wipe off the capillary before the sample fluid is dispensed. This step is especially important if the exterior of the capillary is later brought in contact with a dilution fluid.

To ensure that an exact quantity of fluid is dispensed, it is also advantageous to rinse the capillary with dilution fluid. This step is usually performed while the capillary is immersed in the dilution fluid. The capillary can be rinsed effectively by repeatedly drawing fluid from the vessel into the capillary and ejecting it back into the vessel.

The invention also provides a system for the metered dispensing of sample fluid using the dispensing device described above. In this system, the device is inserted in the collar of a vessel in such a way that the opening in the balloon is closed by the collar and the end-to-end capillary extends into the interior of the vessel. In this embodiment, no requirements must be placed on the opening in the balloon in terms of sufficient flow resistance. The only requirement is that the opening allow air to escape from the interior of the balloon, as is the case with the embodiment described above. However, the opening can be relatively large, because it is closed when inserted in the collar, and flow resistance does not need to be generated by limiting the size of the opening.

The vessel for use with the dispensing device has a collar through which the interior of the vessel can be accessed. The collar can form a one piece unit with the vessel, or the collar can be inserted into an opening in the vessel. The collar and the region of the balloon in which the gas-escape opening is located are designed in such a way that the opening is closed when the balloon is inserted into the collar. This can be accomplished effectively using a collar that has a conical shape that projects toward the vessel interior. When a collar such as this is used, part of the balloon also has a conically projecting shape. To ensure that the opening is sealed properly, the part of the balloon that forms the seal should have a stable shape. This means that the balloon preferably has a first region with thin walls so it can be compressed easily, and a second region that has a higher material strength and is harder to deform.

In a system that has an insertion collar into which the dispensing device can be inserted directly, the insertion collar also has a closure section (e.g., a snap or threaded cap, or a removable sealing foil) or a perforatable membrane that seals off the interior of the vessel. This closure section prevents contamination of the inside of the vessel. This is especially important with vessels filled with a dilution fluid in order to prevent the fluid from escaping.

In an especially preferred embodiment of the invention, the vessel has a closure section with a region that can be opened. The insertion collar is inserted in this area that can be opened. The opening in the closure section of the vessel can be preferably created by the insertion collar during insertion. To accomplish this, the vessel has a receiving area for receiving the insertion collar, the receiving section having a break-off point. The area where the collar is to be inserted can have a membrane that can be punctured or a plate, for instance, that is connected with the closure section by means of a break-off point. When the insertion collar is inserted, the membrane is punctured or the break-off point is broken so that the insertion collar opens a channel between the inside of the vessel and the exterior space. The receiving area of the closure section for attachment of the insertion collar is preferably a guide collar that ensures that the insertion collar is properly positioned in the closure section. It is also advantageous if the insertion collar and the dispensing device have snap-in pieces or the like that snap into the collar when the dispensing device is inserted into the insertion collar and ensure that the insertion collar remains on the dispensing device when the dispensing device is separated from the vessel. Using this embodiment it is especially possible to also use the dispensing device to dispense the dilution fluid that is mixed with the sample fluid.

The present invention therefore also includes a method for dispensing a sample fluid diluted by a predetermined factor that comprises the following steps:

The accessible end of the end-to-end capillary of the dispensing device is brought in contact with the fluid to be dispensed so that the capillary fills with fluid, The dispensing device is inserted into an insertion collar located on a vessel containing a defined quantity of dilution fluid in such a way that the opening of the balloon is closed by the insertion collar, The quantity of fluid contained in the capillary is dispensed into the vessel via compression of the balloon, The dilution fluid is mixed with the sample fluid, Diluted sample fluid is drawn into the capillary, The dispensing device is removed from the vessel and the insertion collar preferably remains attached to the dispensing device, Diluted sample fluid is dispensed via compression of the balloon of the dispensing device.

BRIEF DESCRIPTION OF DRAWINGS

The present invention is explained in greater detail using the following figures:

FIG. 1: Dispensing device

FIG. 2: System for metered dispensing of sample fluids

FIG. 3: System before use

FIG. 4: Vessel opening

DETAILED DESCRIPTION OF THE INVENTION

Figure 5:
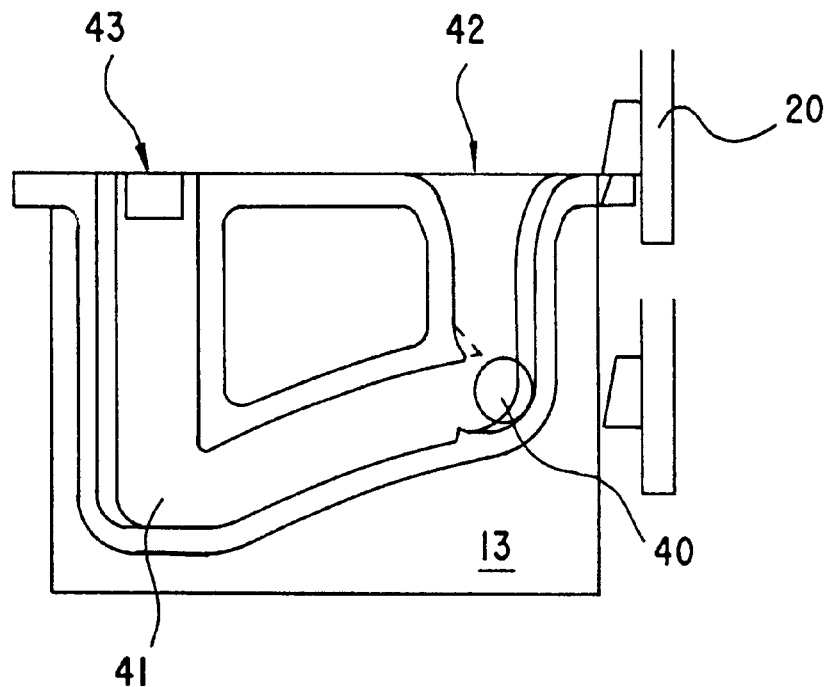
FIGS. 5 and 6: View of the exterior circumferential surface of the closure section area before (FIG. 5) and after (FIG. 6) the system has been opened

A dispensing device (1) is shown in FIG. 1. The device shown includes a balloon (2), the upper section of which is compressible. The lower section of the balloon has two openings (4). In this section, the balloon to be used in the system described below is preferably made of harder material than in the upper section so that it retains its shape. Moreover, the lower section of the balloon has an opening in which an end-to-end capillary (3) is inserted. A holding device (5) is attached to the upper section of the balloon that is used for handling. If the holding device has hollow spaces, as shown in this example, it must be ensured that these hollow spaces do not communicate with the interior of the balloon to avoid pressure fluctuations in the balloon created when the holding device is handled.

FIG. 2 shows a system of a dispensing device according to FIG. 1 and a vessel (10) containing a fluid (12). The vessel has a closure section (13) into which an insertion collar (11) is located. The lower section of the dispensing device is inserted into the insertion collar in such a way that the openings (4) are closed.

The figures below illustrate an especially preferred system. FIG. 3 shows this system in its resting state, before use. The balloon (2) is inserted in a cylinder located in the upper section of a cap (20). The system is designed so that the end-to-end capillary extends into the cap (20) and is therefore protected from contamination and damage. The cap (20) abuts an insertion collar (21) that is inserted loosely into a guide collar (22). The guide collar is part of the closure section (13). A sealing plate (23) is located on the side of the guide collar (22) facing the inside of the vessel that is connected with the guide collar (22) by means of break-off points. The sealing plate (23) is a section of the closure section that can be opened when the system is used. FIG. 4 shows how this is done. Before the closure section is opened, the dispensing device is removed from the cap (20) (see arrow (30)). Subsequently the cap (20) is turned while the vessel (10) remains stationary (see arrow (31)). Hereby the cap (20) is turned toward the vessel (10), pressing the insertion collar (21) toward the interior of the vessel, removing the sealing plate (23) and breaking the break-off points. This causes the insertion collar (21) to enter into a press fit with the guide collar (22) so that gas can no longer escape between the insertion collar and the guide collar, ensuring that the interior of the vessel communicates with the exterior space only by means of the insertion collar (21). The movement of the cap (20) toward the vessel (10), which is performed by turning the cap, can be accomplished by means of a screw thread, for instance. In this case, however, a mechanism has been proven to be especially advantageous. This mechanism is shown in greater detail in FIGS. 5 and 6.

Figure 6:
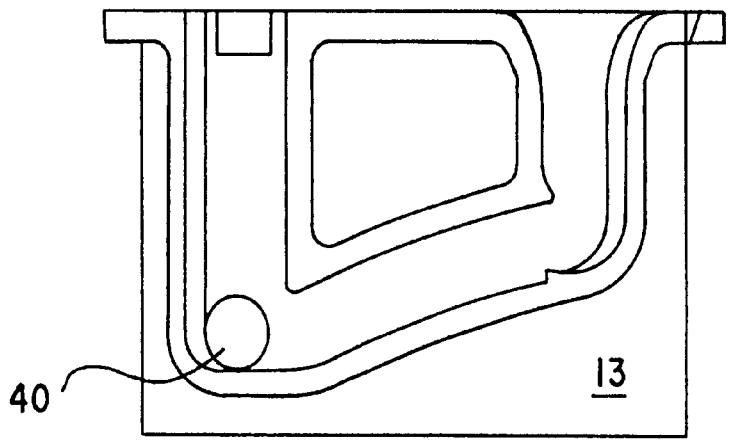

FIG. 5 corresponds to FIG. 3, i.e., it represents the position before the system is used. Accordingly, FIG. 6 corresponds to FIG. 4. FIG. 5 shows the external circumferential surface of the closure section (13) along with part of the cap (20). A peg (40) that engages in the groove (41) on the circumferential surface of the closure section is located on the interior surface of the cap (20). The groove (41) has two openings. The first opening (42) makes it possible to sit the cap (20) on the closure section (13) in such a way that the peg (40) catches in the groove (41). When the cap (20) is turned relative to the vessel and, therefore, the closure section (13), remains stationary, the peg (40) is brought into the position shown in FIG. 6. The diagonal trajectory of the groove between the positions of the peg shown causes the cap (20) to move toward the vessel (10). The second opening (43) in the groove makes it possible for the cap (20) to be removed from the closure section (13) after it has been turned. This makes the insertion collar accessible for insertion of the dispensing device.

Figure 7:
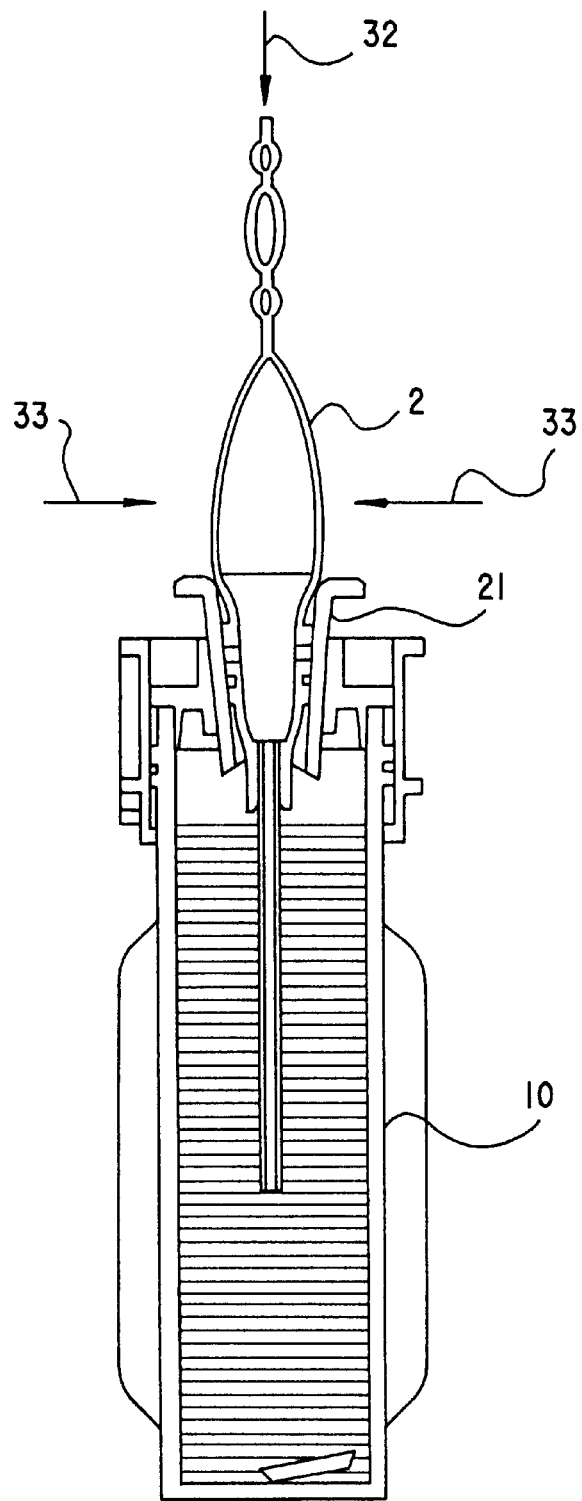
FIG. 7: Dispensing sample fluid into the vessel

After the cap (20) has been removed from the closure section (13), the dispensing device is inserted in the insertion collar (21) as shown by an arrow (32) in FIG. 7. However, before the dispensing device is inserted, sample fluid is drawn into the capillary (3) as shown in FIG. 1. After insertion, the upper section of the balloon (2) is compressed (see arrow (33)), which causes the sample fluid contained in the capillary to be dispensed into the vessel (10). As shown in FIG. 7, the lower section of the balloon with the insertion collar (21) enters into a press fit and the openings in the balloon located in this section are closed.

Figure 8:
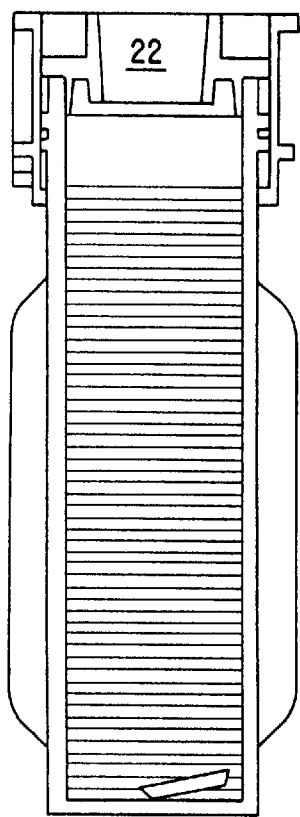
FIG. 8: Vessel after the dispensing device is removed

When the dispensing device is removed from the vessel (10), the insertion collar (21) preferably remains on the balloon so that the vessel remains in the form shown in FIG. 8.

Figure 9:
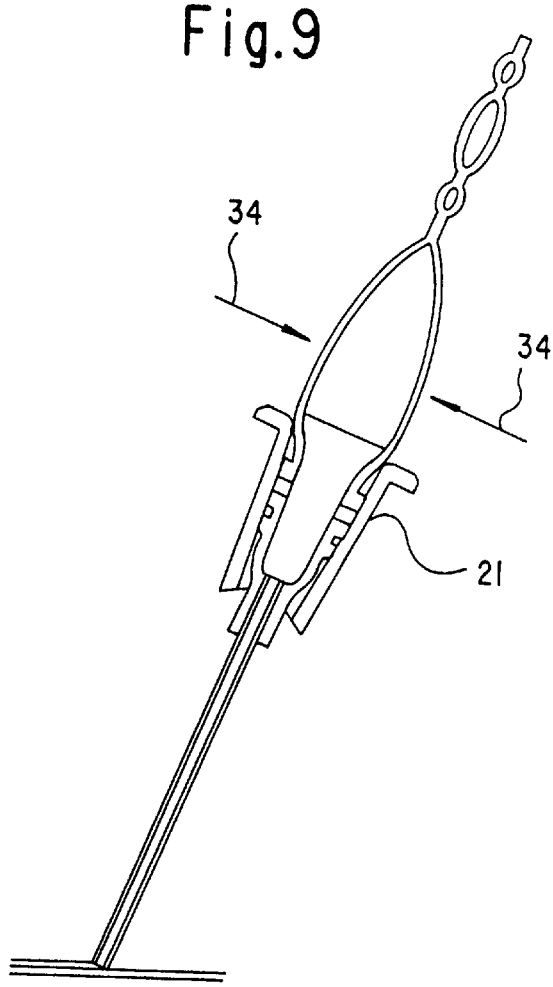
FIG. 9: Dispensing diluted sample fluid using the dispensing device

The dispensing device with the still-attached insertion collar (21) is shown in FIG. 9. By compressing the upper section of the balloon (see arrow (34)), diluted sample fluid can be applied to a microscope slide or the like.

Figure 10:
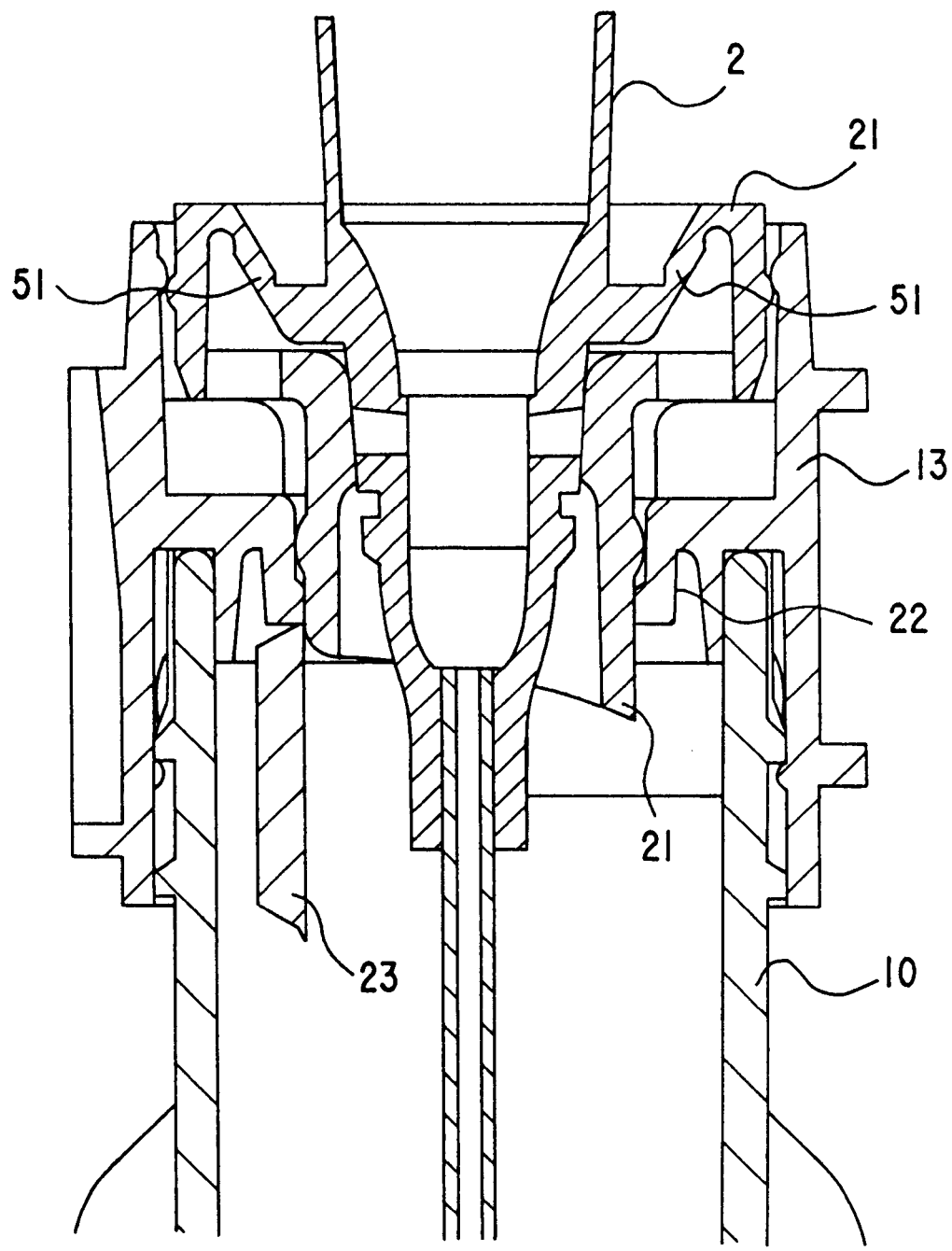
FIG. 10: Detailed view of vessel closure section, insertion collar, and section of the dispensing device in which the opening is located.

The insertion collar (21) can be caused to remain attached to the dispensing device, for instance, by ensuring that the static friction between the dispensing device and insertion collars is greater than between the insertion collar and the guide collar. Snap-in elements are preferably provided, however, that ensure that the insertion collar is removed from the vessel along with the dispensing device. This is illustrated in greater detail in FIG. 10. A circumferential ridge (50) is located on the lower section of the balloon (2) that slides past the snap-in pieces (51) when the balloon is inserted into the insertion collar (21), and then snaps into the position shown in FIG. 10. This design ensures that the sealing function of the insertion collar for the balloon openings is separate from the snap-in function. Accordingly, both functions can be improved separately during development of the dispensing device.

We claim:

1. A dispensing device for dispensing small quantities of sample fluid comprising
   (a) a compressible balloon having an interior space, at least one wall and at least one opening through which the interior space communicates with the exterior of the balloon, said at least one opening having a flow resistance;
   (b) a capillary inserted through said at least one wall of the balloon, wherein said capillary comprises two ends with the first end communicating with said interior space and the second end extending to the exterior of the balloon;

wherein, when said capillary holds the sample fluid and the balloon is compressed, said flow resistance assists the sample fluid to be expelled from the capillary; and (c) a holding device, wherein the handling of the holding device has no effect on the pressure in the interior space of said balloon.

2. The dispensing device of claim 1, wherein said capillary has an exterior surface, which capillary is inserted through said at least one wall of the balloon at the location of said at least one opening leaving a channel adjacent to said exterior surface to form said at least one opening.

3. The dispensing device of claim 1, wherein said at least one opening has a diameter of about 0.001 to 3 mm$^2$.

4. The dispensing device of claim 1, wherein said at least one opening is proximate the first end of said capillary allowing said first end to be viewed through said at least one opening in order to determine when the capillary is completely filled with said sample fluid.

5. The dispensing device of claim 1, wherein said balloon has a volume of about 50 $\mu$l to 20 ml.

6. The dispensing device of claim 1, wherein said capillary has a volume of about 1 $\mu$l to 200 $\mu$l.

7. The dispensing device of claim 1, wherein said at least one opening comprises an opening means for (a) allowing air to escape the interior space of the balloon when the capillary is being filled with the sample fluid, thereby equilibrating air pressure inside the interior space with atmospheric pressure to facilitate the filling of the capillary; and (b) at least partially sealing the balloon against the escape of air when the balloon is compressed to expel the sample fluid from the capillary.

8. A system for diluting a sample fluid, comprising (1) a dispensing device of claim 1, and (2) a vessel means for receiving the sample fluid when the dispensing device dispenses the sample fluid, said vessel means containing at least one dilution fluid.

9. A method for diluting a sample fluid, comprising the following steps (i) providing the system of claim 8, (ii) bringing the second end of said capillary in contact with the sample fluid to fill the capillary with the sample fluid by capillary forces; and thereafter (iii) compressing the balloon to dispense the sample fluid contained in said capillary into the vessel means to create a mixture of the sample fluid and said at least one dilution fluid.

10. The method of claim 9, further comprising, after step (iii), repeatedly drawing up said mixture from said vessel means into the capillary and dispensing said mixture back into said vessel means to rinse said capillary, thereby creating a diluted sample fluid in said vessel.

11. A method for dispensing a sample fluid, comprising the following steps (A) providing a dispensing device of claim 1;

(B) bringing the second end of said capillary in contact with the sample fluid to fill the capillary with said sample fluid by capillary forces; and thereafter (C) compressing said balloon to dispense the sample fluid contained in the capillary.

12. The method of claim 11, further comprising wiping the exterior of the capillary between steps (A) and (B).

13. A method for dispensing a sample fluid; comprising the following steps (A) providing a dispensing device of claim 1

(B) handling said dispensing device using said holding device to bring the second end of said capillary in contact with the sample fluid in order to fill the capillary with said sample fluid by capillary forces; and thereafter (C) compressing said balloon to dispense the sample fluid contained in the capillary.

14. A system for the metered dispensing of a sample fluid, comprising (1) a dispensing device comprising (1) a compressible balloon having an interior space, at least one wall and at least one opening through which the interior space communicates with the exterior of the balloon and (2) a capillary inserted through said at least one wall of the balloon at a location different from said at least one opening, which capillary comprises two ends with the first end communicating with said interior space of the balloon and the second end communicating with the exterior of the balloon; and (II) a vessel having an interior and a closure section, which closure section comprises a collar, wherein the balloon of said dispensing device is insertable into said collar with (1) fluid flow through said at least one opening of the balloon at least substantially restricted by the collar, (2) the second end of said capillary extending into the interior of the vessel; and (3) a portion of the balloon exposed to digital compression to expel the sample fluid from the dispensing device into the vessel.

15. The system of claim 14, wherein the vessel contains at least one fluid for dilution of said sample fluid.

16. The system of claim 14, wherein said dispensing device further comprises a holding device, the handling of which holding device has no effect on the pressure inside the balloon.

17. A method for dispensing a sample fluid, comprising the following steps (A) providing the system of claim 14;

(B) bringing the second end of the capillary in contact with a sample fluid to fill the capillary with said sample fluid by capillary forces with said at least one opening being unrestricted;

(C) inserting the dispensing device into said collar with fluid flow through said at least one opening substantially restricted by said collar and with said second end of the capillary extending into the interior said vessel; and thereafter (D) compressing the balloon to dispense said sample fluid contained in the capillary into said vessel.

18. A system for the metered dispensing of a sample fluid, comprising (1) a dispensing device comprising (i) a compressible balloon having an interior space, at least one wall and at least one opening through which the interior space communicates with the exterior of the balloon, and (ii) a capillary having two ends, which capillary is inserted through said at least one wall of said balloon at a location different from said at least one opening, with the first end of the capillary communicating with the interior space of the balloon and the second end of the capillary communicating with the exterior of the balloon;

(II) a vessel having an interior and a closure which includes an openable section; and (III) an insertion collar proximate said closure of the vessel, through which insertion collar said dispensing device can be inserted into the vessel after the insertion collar is moved toward the openable section of said closure to push open the openable section in order to allow access to the interior of the vessel.

19. The system of claim 18, wherein the closure further comprises a guide collar to guide the movement of the insertion collar.

20. The system of claim 18, wherein the openable section comprises a perforatable membrane, a flap, a stopper or a section with at least one break-off point.

21. The system of claim 18, wherein the dispensing device is inserted into the insertion collar with fluid flow through said at least one opening at least substantially restricted by the insertion collar.

22. The system of claim 21, wherein the dispensing device and insertion collar are securely attached when the dispensing device is inserted into the insertion collar to ensure that the insertion collar remains attached to the dispensing device when the dispensing device is separated from the vessel.

23. The system of claim 21, wherein the wall around said at least one opening of the balloon comes in press contact with the insertion collar when the dispensing device is inserted into the insertion collar, whereby fluid flow through said at least one opening is at least substantially restricted.

24. The system of claim 18, further comprising a cap situated on the closure with the cap abutting the insertion collar, wherein when the cap is moved toward the vessel the cap pushes the insertion collar, which insertion collar in turn pushes the openable section of said closure toward the interior of the vessel, thereby opening the vessel.

25. The system of claim 24, wherein the cap has a thread on the inside surface, which thread catches a counterthread located on the closure, wherein when the cap is turned the thread guides the cap to move toward the vessel.

26. The system of claim 24, wherein the inside surface of the cap comprises at least one peg and the closure further comprises a circumferential surface and a groove on the circumferential surface, with said at least one peg catches said groove.

27. The system of claim 26, wherein, when the cap is turned on top of the vessel, the groove and said at least one peg guide the cap to push the insertion collar toward the interior of the vessel, which insertion collar in turn pushes the openable section of the closure toward the interior of the vessel, thereby opening the vessel.

28. The system of claim 27, wherein the vessel has an axis, and the groove on the closure comprises two branches basically running parallel to the axis of the vessel, which two branches are connected by a branch running substantially diagonal to the axis of the vessel.

29. The system of claim 26, wherein the groove on the closure is open in one site to allow said at least one peg of the cap to be inserted into said groove.

30. The system of claim 29, wherein the groove is open in a second site to allow the cap to be removed from the closure after the cap is turned on top of the vessel.

31. The system of claim 24, wherein the inside surface of the cap comprises a groove and the closure further comprises a circumferential surface and at least one peg on said circumferential surface, with said at least one peg catches said groove.

32. The system of claim 31, wherein, when the cap is turned on top of the vessel, the groove and said at least one peg guide the cap to push the insertion collar toward the interior of the vessel, which insertion collar in turn pushes the openable section of the closure toward the interior of the vessel, thereby opening the vessel.

33. The system of claim 32, wherein the vessel has an axis, and the groove of the cap comprises two branches basically running parallel to the axis of the vessel, which two branches are connected by a branch running substantially diagonal to the axis of the vessel.

34. The system of claim 31, wherein the groove of the cap is open in one site to allow said at least one peg of the closure to be inserted into said groove.

35. The system of claim 34, wherein the groove is open in a second site to allow the cap to be removed from the closure after the cap is turned on top of the vessel.

36. The system of claim 24, wherein the cap has a shaft into which the dispensing device is insertable to entirely enclose the capillary in the shaft.

37. A method for dispensing a sample fluid diluted by a predetermined dilution factor, comprising the following steps (a) providing the system of claim 36, wherein said vessel contains a prescribed quantity of at least one dilution fluid and said closure further comprises a guide collar, with said dispensing device inserted into the shaft of the cap;

(b) removing the dispensing device from the cap;

(c) moving the cap toward the vessel to push the insertion collar toward the interior of the vessel, which insertion collar in turn pushes the openable section of said closure toward the interior of the vessel, thereby opening the vessel and causing the insertion collar to enter into a press fit with the guide collar, ensuring that the interior of the vessel communicates with the exterior of the vessel only by means of the insertion collar;

(d) removing the cap from the closure;

(e) bringing the second end of the capillary of the dispensing device in contact with said sample fluid to fill the capillary with said sample fluid by capillary forces with said at least one opening being unrestricted;

(f) inserting the dispensing device into the insertion collar by placing the second end of the capillary in the vessel interior, which insertion collar at least substantially restricts fluid flow through said at least one opening of the balloon;

(g) compressing the balloon to dispense said sample fluid contained in the capillary into the vessel to create a mixture;

(h) further mixing the mixture by shaking the vessel and/or repeatedly drawing up the mixture from the vessel into the capillary and dispensing said mixture back into the vessel to create a further mixed fluid;

(i) drawing the further mixed fluid into the capillary;

(j) removing the dispensing device from the vessel; and thereafter (k) compressing the balloon to dispense the further mixed fluid in the capillary, thereby dispensing the sample fluid diluted by the predetermined dilution factor.

38. A method for dispensing a sample fluid, comprising the following steps (a) providing the system of claim 18;

(b) bringing the second end of the capillary of the dispensing device in contact with said sample fluid to fill the capillary with said fluid by capillary forces with said at least one opening being unrestricted;

(c) inserting the dispensing device into the insertion collar by placing the second end of the capillary in the vessel interior, which collar substantially restricts fluid flow through said at least one opening of the balloon; and thereafter (d) compressing the balloon to dispense said sample fluid contained in the capillary into the vessel.

39. The method of claim 38 for dispensing the sample fluid into at least one dilution fluid, wherein the vessel contains said at least one dilution fluid, said method further comprising the following step after step (d):

mixing the sample fluid dispensed into the vessel and said at least one dilution fluid by shaking the vessel and/or repeatedly drawing up a mixture of the dispensed sample fluid and said dilution fluid from the vessel into the capillary and dispensing said mixture back into the vessel to rinse said capillary.

40. A method for dispensing a sample fluid diluted by a predetermined dilution factor, comprising the following steps (a) providing the system of claim 18, wherein said vessel contains a prescribed quantity of at least one dilution fluid;

(b) bringing the second end of the capillary of the dispensing device in contact with said sample fluid to fill the capillary with said sample fluid by capillary forces with said at least one opening being unrestricted;

(c) inserting the dispensing device into the insertion collar by placing the second end of the capillary in the vessel interior, which collar at least substantially restricts fluid flow through said at least one opening of the balloon;

(d) compressing the balloon to dispense said sample fluid contained in the capillary into the vessel to create a mixture;

(e) further mixing the mixture by shaking the vessel and/or repeatedly drawing up the mixture from the vessel into the capillary and dispensing said mixture back into the vessel to create a further mixed fluid;

(f) drawing the further mixed fluid into the capillary;

(g) removing the dispensing device from the vessel; and thereafter (h) compressing the balloon to dispense the further mixed fluid in the capillary, thereby dispensing the sample fluid diluted by the predetermined dilution factor.

* * * * *